United States Patent [19]

Arretz et al.

[11] Patent Number: 5,767,229
[45] Date of Patent: Jun. 16, 1998

[54] PROCESS FOR THE PREPARATION OF ORGANIC DISULPHIDES AND POLYSULPHIDES IN THE PRESENCE OF POLYSTYRENE-DIVINYL-BENZENE (PS-DVB) RESINS POSSESSING GUANIDINE OR AMIDINE GROUPS

[75] Inventors: Emmanuel Arretz; Frédéric Lopez, both of Pau, France

[73] Assignee: Elf Aquitaine Production, France

[21] Appl. No.: 764,016

[22] Filed: Dec. 11, 1996

[30] Foreign Application Priority Data

Dec. 11, 1995 [FR] France .................... 95 14582

[51] Int. Cl.⁶ .................... C08G 75/04
[52] U.S. Cl. .................... 528/374; 568/21; 568/26
[58] Field of Search .................... 568/21, 26; 528/374

[56] References Cited

U.S. PATENT DOCUMENTS

| | | |
|---|---|---|
| 3,308,166 | 3/1967 | Biensan et al. |
| 3,856,715 | 12/1974 | Corte et al. |
| 4,623,711 | 11/1986 | Morris et al. .................... 528/375 |
| 5,028,259 | 7/1991 | Lin et al. .................... 75/722 |
| 5,068,445 | 11/1991 | Arretz .................... 568/21 |

OTHER PUBLICATIONS

Tomoi et al., "Polystyrene-supported 1.8-diazabicyclo [5.4.0]undec-7-ene as . . . ", *Macromol. Chem.*, 185:2117-2124, 1984.
Iijima et al., "Polymer-Supported Bases.XI.Esterification and Alkylation in the . . . ", *J.M.S.-Pure Appl. Chem.*, A29(3):249-261, 1992.
Chemical Absracts, vol. 104, No. 12, Abstract No. 90051k, 24 Mar. 1986.

Primary Examiner—Melvyn I. Marquis
Assistant Examiner—D. Aylward
Attorney, Agent, or Firm—Millen, White, Zelano & Branigan, P.C.

[57] ABSTRACT

In a process for the preparation of organic disulphides and polysulphides by reaction of sulphur with a mercaptan or with a polysulphide of lower sulphur order in order to convert it into polysulphide of higher order, or alternatively by reaction of a mercaptan with an organic polysulphide of a high sulphur order in order to convert it into a polysulphide of lower sulphur order, in the presence of a catalyst in the form of a resin with a basic function, the resin is based on a polystyrene-divinyl benzene support functionalized with guanidine or amidine groups, and the reaction is preferably conducted in the presence of methanol.

27 Claims, No Drawings

PROCESS FOR THE PREPARATION OF ORGANIC DISULPHIDES AND POLYSULPHIDES IN THE PRESENCE OF POLYSTYRENE-DIVINYL-BENZENE (PS-DVB) RESINS POSSESSING GUANIDINE OR AMIDINE GROUPS

CROSS REFERENCE TO RELATED APPLICATIONS

This application is related to Attorney Docket No. ATOCM 68, application Ser. No. 08/764,017 filed Dec. 11, 1996, entitled "Process for the Preparation of Resins with a Primary Amine or Guanidine Function, and Resins Thus Obtained" by LePerchec, Abiuso, and Arretz, based on French Priority application 95/14583 filed Dec. 11, 1995, and Attorney Docket No. ATOCM 70, application Ser. No. 08/764,012 filed Dec. 11, 1996, entitled "Process for the Preparation of Organic Disulphides and Polysulphides in the Presence of Polystyrene-Divinyl-Benzene Resins Possessing Primary Amine Groups" by Arretz, based on French Priority application 95/14581 filed Dec. 11, 1995, all of these applications being incorporated by reference herein.

BACKGROUND OF THE INVENTION

The present invention relates to the production of organic disulphides and polysulphides $R—S_n—R$ (with $n \geq 2$) by reaction of mercaptans with sulphur in the presence of basic resins which act as catalysts, according to the reaction:

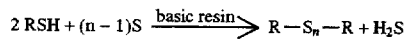

$$2\,RSH + (n-1)S \xrightarrow{\text{basic resin}} R—S_n—R + H_2S$$

In the presence of these same basic resins, organic disulphides and polysulphides of low sulphur order can be converted into polysulphides of higher sulphur order by reaction with sulphur. Similarly, in the presence of these same basic resins, organic polysulphides of high sulphur order can be converted into polysulphides of lower sulphur order by reaction with mercaptans.

Thus, patent application EP-A-337,837 teaches the preparation of organic disulphides and polysulphides in the presence of organic anion exchange resins containing tertiary amine or quaternary ammonium functional groups (active in OH⁻ form). Such resins, generally in the form of grains or beads which are insoluble in liquid reaction media and are thus easy to separate out at the end of the reaction, allow polysulphides and organic disulphides to be obtained by reaction of elemental sulphur with mercaptans and also allow organic polysulphides of high sulphur order to be obtained by reaction of elemental sulphur with organic polysulphides of lower sulphur order.

S. V. Luis, M. I. Burguete and B. Altava, Reactive & Functional Polymers, 26, 1995, 75–83, indicate that the ready chloromethylation of polystyrene resins and the high reactivity of the resulting benzyl sites allows the introduction of a large number of functional groups and explains the widespread use of these polymers.

On the other hand, these authors remark that the reduced length of the methylene spacer arm reduces the mobility of the functional groups introduced and, in certain cases, makes it difficult for reactants, substrates and solvents to gain access to them. This situation may lead to a decrease in the activity of the functional groups when they are compared with their soluble correspondents. In certain cases, a marked improvement in the activity of these groups bound to the resin has been obtained when the active site is separated from the polymer skeleton by a suitable spacer arm.

S. V. Luis et al. prepare polystyrene resins having spacer arms in the form of a linear aliphatic chain containing 6 or 9 methylene groups and bearing a hydroxyl group —OH at the end of the chain. This hydroxyl group is converted into a tosylate leaving group, the latter being replaced by substitution with a tertiary amine group.

In this synthesis, S. V. Luis et al. use functionalization of the polystyrene resin by a Friedel Crafts type reaction using the acid chloride derived from a monoalkyl ester of an alkanedioic acid.

This synthesis has the major drawback of reducing both a tosylhydrazone group and an ester group by double hydride ($LiAlH_4$) in tetrahydrofurane (THF). This reduction makes this synthetic route unattractive in terms of a large-scale industrial development of resins containing these $C_6$ or $C_9$ spacer arms.

Other authors have become interested in producing spacer arms in the form of a methylene chain. Thus, M. Tomoi, N. Kori and H. Kakiuchi, Reactive Polymers, 3, 1985, 341–349, introduce a long aliphatic chain onto polystyrene resins by alkylation with ω-bromoalkenes in the presence of trifluoromethanesulphonic acid.

However, this synthesis is limited to the preparation of polymers with a spacer arm which have a low degree of crosslinking (0–4%).

In the document Makromol. Chem 185, 1984, 2117–2124, M. Tomoi, Y. Kato and H. Kakiuchi carried out the synthesis of resins functionalized with a radical comprising a bicyclic amidine:

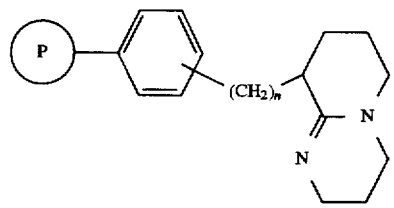

with n being an integer equal to 1, 4 or 7.

These amidine resins (when n is 4 or 7) were prepared from ω-bromoalkyl microporous resins, which are themselves obtained from ω-bromoalkylstyrene and divinylbenzene.

In a similar manner, in the document J.M.S. Pure Appl. Chem., A29(3), pp 249–261 (1992), K. IIjima, W. Fukuda, and M. Tomoi carried out the synthesis of a microporous resin functionalized with a radical comprising a bicyclic guanidine:

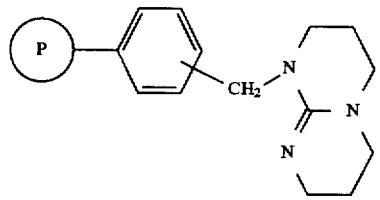

These authors studied the activity of the above bicyclic amidine resin (n=1) and of the above guanidine resin in the esterification of benzoic acid with 1-bromobutane in toluene or acetonitrile.

These two resins have proven to be effective in the alkylation with 1-bromobutene of compounds containing active methylene.

Starting with a chloromethyl polystyrene resin, G. D. Darling and M. J. Fréchet, J. Org. Chem., 51, 1986, 2270–2276 have, for their part, obtained a spacer arm —(CH$_2$)$_2$— which separates the resin from a hydroxyl —OH at the end of the chain. This hydroxyl is converted into tosylate and then, via the Gabriel reaction using potassium phthalimide and lastly with hydrazine, into primary amine. However, this synthesis has the drawback of using n-butyllithium or lithium aluminium hydride.

SUMMARY OF THE INVENTION

A principal object the present invention is to provide a process for the preparation of organic disulphides and polysulphides, according to the reactions outlined above, in the presence of functionalized and specially selected or synthesised PS-DVB resins, in order to obtain better results than those of the prior art. These better results may be, for example, a better degree of conversion of the reactants and/or faster reaction kinetics.

Upon further study of the specification and claims, further objects and advantages of this invention will become apparent to those skilled in the art.

These objects are achieved by the use of resins functionalized with guanidine or amidine groups.

More precisely, the present invention provide a process for the preparation of organic disulphides and polysulphides by reaction of sulphur with a mercaptan or with a polysulphide of lower sulphur order in order to convert it into a polysulphide of higher order, or alternatively by reaction of a mercaptan with an organic polysulphide of a high sulphur order in order to convert it into polysulphide of a lower sulphur order, in the presence of a catalyst in the form of a resin with a basic function, characterised in that the resin is based on polystyrene-divinylbenzene (PS-DVB), functionalized with basic groups and having the general formula (I):

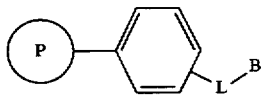

(I)

wherein:
B represents a group chosen from:
1.—a guanidine radical of general formula (C):

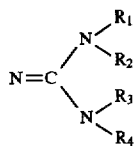

(C)

substituted by L on the imine nitrogen, in which R$_1$, R$_2$, R$_3$ and R$_4$ are, independently of each other, chosen from hydrogen and methyl, ethyl, propyl, butyl, cyclohexyl and phenyl groups, with the condition that L in this case represents a linear organic radical which is as long as or longer than the methylene radical —CH$_2$—.

2.—a cyclic guanidine radical of formula (D):

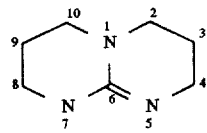

(D)

substituted by L at the 7-position, with the condition that L in this case represents a radical —(CH$_2$)$_n$—, n being an integer equal to 1 or 3 to 9.

3.—a cyclic amidine of formula (E):

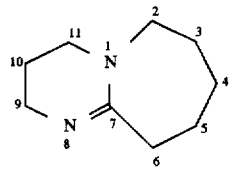

(E)

substituted by L at the 6-position, with the condition that L in this case represents a radical —(CH$_2$)$_n$—, n being an integer equal to 1 or 3 to 9.

4.—a cyclic amidine of formula (F):

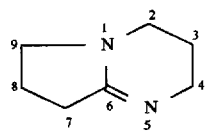

(F)

substituted by L at the 7-position, with the condition that L in this case represents a radical —(CH$_2$)$_n$—, n being an integer equal to 1 or 3 to 9; and

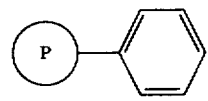

represents the PS-DVB resin support.

The resins which serve as starting materials for the preparation of the resins of general formula (I) may be PS-DVB copolymers or chloromethyl PS-DVB copolymers.

With a low content of divinylbenzene (0.5 to 7% by weight) as crosslinking agent, copolymers of the gel type are obtained, whereas with higher DVB contents, macrocrosslinked resins of macroporous structure may be obtained.

The DVB content may be from 0.5% to 60% by weight relative to the total weight of the PS-DVB copolymer.

The starting materials and, consequently, the resins of general formula (I) may be of gel type; preferably, however, the resins of general formula (I) are macrocrosslinked and of macroporous structure, since these characteristics generally entail a better catalytic activity in the process.

These PS-DVB resins may be chloromethylated with chloromethyl ether, according to known techniques which are described in the literature, to variable chlorine (Cl) contents, generally from 1 to 20% by weight of chlorine relative to the weight of chloromethyl resin.

Preferably, the radical L represents methylene. This is because these resins are easy to synthesize.

Advantageously, the radical L has the general formula (II) below:

—CH$_2$—(X—CH$_2$—CH$_2$)$_m$—  (II), in which X represents oxygen or sulphur and m is equal to 1 or 2.

Preferably, in the formula (II), X is oxygen and m is equal to 1, or alternatively X is sulphur and m is equal to 1.

Advantageously, the mercaptans and organic disulphides and polydisulphides have hydrocarbon radicals R chosen from an alkyl, cycloalkyl, aryl, aralkyl and alkylaryl group.

The present invention applies in particular to the production of dialkyl disulphides and polysulphides containing in total from 2 to 40 carbon atoms, for example dimethyl, diethyl, dipropyl, dibutyl, dipentyl, dihexyl, diheptyl, dioctyl, didecyl and didodecyl disulphide and polysulphides.

The invention also applies to the preparation of cycloalkyl disulphides and polysulphides, for example dicyclohexyl disulphide or polysulphides, or to the preparation of diphenyl disulphide or polysulphides, for example.

Advantageously, the hydrocarbon radical R bears one or more functional groups. These groups are, for example, halogen atoms, —OH, —OR', —SR', —NR'R", CN, —CHO, —COR' and —COOR'. R' and R" denoting $C_1$ to $C_{12}$ aliphatic radicals or cycloaliphatic, aromatic or alkylaromatic radicals.

The catalytic activity of the resins used in the present invention is displayed at very low resin contents in the mixtures.

Advantageously, the resin is present in an amount ranging from 0.01 to 20 parts by weight per 100 parts by weight of reaction mixture, including resin.

The process according to the invention uses a reaction which may be carried out at a temperature of from −10° C. to 150° C. Preferably, the temperature is from +10° C. to 120° C.

The reactions may be performed at atmospheric pressure or at higher pressures which may reach 50 bar. In general, this pressure is 28 bar absolute. In the case of relatively non-volatile reactants of low vapour pressure, the reaction may be performed at pressures below atmospheric pressure, optionally in the presence of an inert gas, such as nitrogen.

The mercaptan/sulphur molar ratio depends on the nature of the mercaptan used and on the product to be prepared (disulphide or polysulphide). Advantageously, this ratio is from 0.3 to 10 and preferably from 0.4 to 6.

In the case where an organic polysulphide of high sulphur order is used at the start, which it is desired to convert into organic polysulphide of low sulphur order, for example into trisulphide R—$S_3$—R or disulphide R—$S_2$—R by the action of the corresponding mercaptan, advantageously, a mercaptan/polysulphide molar ratio ranging from 2 to 10 is used.

The production of organic disulphides or polysulphides in the presence of PS-DVB resins with a guanidine or amidine function may be carried out in a stirred or tubular reactor, according to a batchwise process, or by loading the reactants before reacting them, or by gradual addition of one of the reactants, or by simultaneous addition of the reactants into the reactor, or alternatively according to a continuous process with controlled addition of the reactants.

In the case where sulphur is one of the reactants (the other being a mercaptan or a polysulphide of low sulphur order), it may be introduced in liquid or solid form.

The resins of general formula (I) may be obtained or prepared in the following way:

1. The group B is a radical of general formula (C).

A process which consists in substituting the chlorine of a chloromethyl polystyrene-divinylbenzene resin with a substituted or unsubstituted guanidine is known from U.S. Pat. No. 5,340,380, this process making it possible to obtain resins of general formula (I.C):

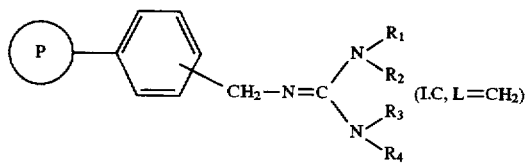 (I.C, L=CH₂)

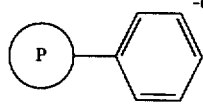
-continued representing the starting solid polystyrene-divinylbenzene resin support it being possible for $R_1$, $R_2$, $R_3$ and $R_4$ each to be a hydrogen, an alkyl group or an aromatic group.

Thus, U.S. Pat. No. 3,346,516 describes this technique of functionalization by reaction of a chloromethyl polystyrene-divinylbenzene resin with guanidine or tetramethylguanidine in the presence of a lower alcohol and a solvent for swelling the copolymer, such as tetrahydrofuran, dioxane or diglyme.

In U.S. Pat. No. 5,028,259, tetramethylguanidine is placed in contact with a chloromethyl polystyrene-divinylbenzene resin in a mixture of toluene and tetrahydrofuran.

In U.S. Pat. No. 5,340,380, guanidines are reacted with chloromethyl resins of this same type in the presence of sodium hydroxide in a solvent consisting of ethanol or water.

However, this technique of functionalization of chloromethyl PS-DVB resin with a guanidine is very limited in practice for the production of resins of formula (I.C) in which the guanidine radicals bear $R_1$ to $R_4$ substituents other than four methyls or four hydrogens, insofar as only guanidine and 1,1,3,3-tetramethylguanidine are currently commercial.

Such resins (I.C) in which the groups $R_1$ to $R_4$ are all other than hydrogen may be obtained by using tetrasubstituted ureas, which are often marketed, under the following preparation conditions:

a) to begin with, a PS-DVB resin functionalized with primary amine groups and having the general formula (A) is prepared

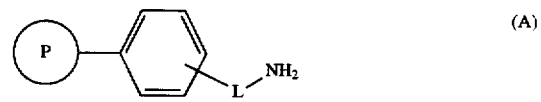 (A)

These may be obtained by various techniques:

1. It is possible, for example, to start with a resin of general formula (J):

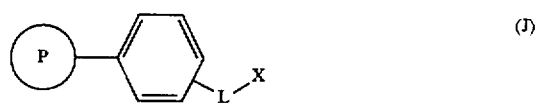 (J)

X being a leaving group, in particular halogen or tosylate which may be obtained from a hydroxyl group —OH, and L having the same meaning as above, in particular a radical —(CH₂)$_p$—, with p being an integer from 1 to 9, including 2.

Preferably, when L represents a single methylene, X is a chlorine atom. In this case, a method, described by D. H. Rich and S. K. Gurwara, J. Am. Chem. Soc., 1975, 97-1575–1579, consists in reacting a chloromethyl PS-DVB resin with excess ammonia. Another route is based on the production of phthalimidomethyl PS-DVB resin, which is converted by hydrazinolysis into a resin with a primary amine function. The two methods for gaining access to such phthalimidomethyl resins are described in the publication by A. R. Mitchell, S. B. H. Kent, B. W. Erickson and R. B. Merrifield, Tetrahedron Letters No. 42, 1976, 3795–3798. One consists in starting with a PS-DVB resin which, on reaction with N-(chloromethyl)phthalimide, is converted directly into phthalimidomethyl resin. The other method starts with a chloromethyl PS-DVB resin which is treated with potassium phthalimide to give the corresponding phthalimidomethyl resin.

A few PS-DVB resins with a primary amine function of formula (A) in which L represents a methylene are commercial.

Thus, the company Purolite proposes two macroporous resins, A-107 and A-109, whereas the company Fluka has, in its 1995–1996 catalogue, two gel resins: the resin 08564 PS crosslinked with 2% DVB and containing 1.1 mmol of —$NH_2$ groups per gram of resin, and the resin 08566 PS crosslinked with 1% DVB and containing 0.6 mmol of —$NH_2$ per gram of resin.

The method with potassium phthalimide can also be applied to the resins of formula (J) in the case where L is a linear organic radical longer than the methylene radical, in particular —$(CH_2)_n$—, with n being a number greater than 1.

2. It is also possible to start with a PS-DVB resin of formula (J) in which L represents a methylene and X has the above meaning and preferably represents a chlorine atom. It has been discovered that this chloromethyl resin can be reacted with an alkanolamine or a mercaptoalkylamine, in alkaline alkoxide form, under the Williamson reaction conditions.

If the ethanolamine is used, PS-DVB resins having a primary amine function with —$CH_2$—O—$CH_2$—$CH_2$—$NH_2$ functional groups bound to the PS-DVB resin supports are obtained.

Similarly, starting with 2-aminoethanethiol hydrochloride, —$CH_2$—S—$CH_2$—$CH_2$—$NH_2$ functional groups are obtained.

If 2-(2-aminoethoxy)ethanol is used, PS-DVB resins having a primary amine function with —$CH_2$(O—$CH_2$—$CH_2$)$_2$—$NH_2$ functional groups are obtained.

Lastly, using 2-[(2-aminoethyl)thio]ethanethiol, —$CH_2$—(S—$CH_2$—$CH_2$)$_2$—$NH_2$ functional groups are obtained.

This starting mercaptoalkylamine may be prepared according to Iwakura et al., J. Polym. Sci. Part A, 2, 1964, 881–883 or according to I. Voronkov, M. G. et al., Chem. Heterocycl. Compd. (Engl. Transl.)15, 1979, 1183–1185.

The general conditions of the Williamson reaction are as follows:

The alkanolamine or the mercaptoalkylamine diluted in anhydrous tetrahydrofuran (THF) is reacted with sodium hydride suspended in anhydrous THF. After formation of the sodium alkoxide or the sodium mercaptide, the chloromethyl resin is introduced into the liquid reaction medium.

b) After the resin possessing primary amine groups of general formula (A) is obtained, these groups are reacted with chloroformamidinium chloride (Vilsmeier salt) of general formula (H):

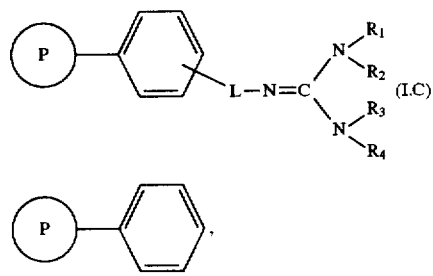

in which $R_1$, $R_2$, $R_3$ and $R_4$ are, independently of each other, chosen from the methyl, ethyl, propyl, butyl, cyclohexyl and phenyl groups, to obtain a PS-DVB resin functionalized with a guanidine group and of general formula (I.C):

L and $R_1$ to $R_4$ having the same meanings as above.

The chloroformamidinium chlorides (H) are generally obtained from tetrasubstituted ureas by reaction with electrophilic compounds such as phosgene, thionyl chloride, oxalyl chloride or phosphorus oxychloride, according to the methods described in the literature, in particular:

| | |
|---|---|
| $COCl_2$ | H. Eilingsfeld, M. Seefelder, Angew. Chem., 72, 1960, 836. |
| $SOCl_2$ | H. Ulrich, A. A. R. Sayigh, Angew. Chem. Intern. Ed. Engl., 5, 1966, 704. |
| $(COCl)_2T.$ | Fujisawa et al., Chem. Lett., 1982, 1891. |
| $POCl_3$ | H. Bredereck, K. Bredereck, Chem. Ber., 94, 1961, 2278. |

Generally, stoichiometric amounts of tetrasubstituted ureas and of electrophilic chloro compounds are used at the start and the process is performed in the presence of a solvent such as carbon tetrachloride in the case of oxalyl chloride, or without solvent with phosgene or thionyl chloride, at a temperature generally of from 0° C. to 40° C., and under an anhydrous atmosphere to prevent any hydrolysis.

The tetrasubstituted ureas are advantageously chosen from tetramethylurea, tetraethylurea, tetra-n-propylurea and tetra-n-butylurea.

The chloroformamidinium chlorides (H) are generally placed in a solvent such as toluene or acetonitrile. Their reactions with the resins containing a primary amine function (A) are carried out in the presence of a base, preferably in the presence of an excess of base.

If the base is triethylamine (TEA), the processes are generally performed with a molar excess of TEA of from 10 to 50% relative to the chloroformamidinium chlorides (H). The latter are generally in a molar excess of from 10 to 100% relative to the number of moles of primary amine function, in order to convert all of the latter into guanidine functions.

2. The group B is a radical of general formula (D)

(a) To start with, a resin of general formula (J) as in point 1. a) above is prepared, L representing a radical —$(CH_2)_n$—, n being an integer equal to 1 or 3 to 9 and X being a chlorine or a bromine.

(b) The above halogenated resin is reacted with 1,5,7-triazabicyclo[4.4.0]dec-5-ene (TBD), in a similar manner to the process of M. Tomoi et al. J.M.S. Pure Appl. Chem. A29(3), 1992, 249–261, in particular page 251 ("Preparation of Polystyrene-Supported TBD").

A PS-DVB resin is thus obtained which is functionalized with a bicyclic guanidine group of general formula (I.D.):

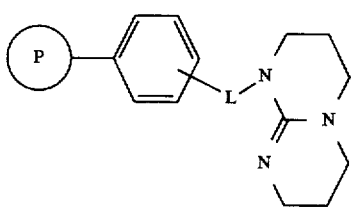

L representing a radical —(CH$_2$)$_n$— with n being an integer equal to 1 or 3 to 9.

3. The group B is a radical of general formula (E)

a) the resin of general formula (J) as in point 2. a) above is prepared to start with.

b) The halogenated resin obtained above is reacted with 1,8-diazabicyclo[5.4.0]undec-7-ene (DBU) in a similar manner to the process of M. Tomoi et al., Makromol. Chem. 185, 1984, 2117–2124, in particular page 2118, "Preparation of polystyrene-supported DBU").

A PS-DVB resin is thus obtained which is functionalized with a bicyclic amidine group of general formula (I.E):

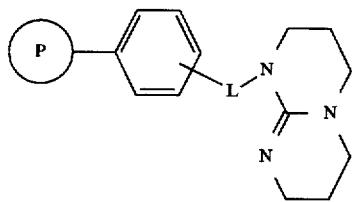

L representing a radical —(CH$_2$)$_n$— with n being an integer equal to 1 or 3 to 9.

3. The group B is a radical of general formula (F). The process is performed as in 2. a) and 2. b) except that the DBU is replaced by 1,5-diazabicyclo[4.3.0]-non-5-ene (DBN).

A PS-DVB resin is thus obtained functionalized with a bicyclic amidine group of general formula (I.F):

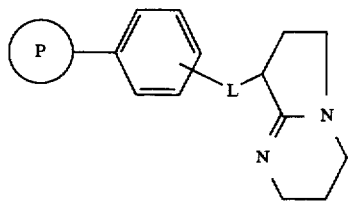

L representing a radical —(CH$_2$)$_n$ with n being an integer equal to 1 or 3 to 9.

The catalytic efficiency of the resins used in the present invention is found to be improved when they are used dry.

The catalytic activity of the resins of gel type, used in the present invention, is greatly improved by the presence of methanol in the reaction mixtures.

This promoting effect of methanol (also observed with ethanol, but to a lesser extent) is detected at and above low contents in the reaction mixtures, for methanol quantities ranging from 0.01 g to 2 g per 100 g of reaction mixture comprising resin, sulphur, mercaptan and methanol or sulphur resin, polysulphide and methanol, or alternatively resin, mercaptan, polysulphide and methanol. Thus, methanol is advantageously added to the reaction medium.

Without further elaboration, it is believed that one skilled in the art can, using the preceding decription, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

Experimental section

The resins are dried under a vacuum of about 4×10$^3$ pascal (Pa).

1. Production of PS-DVB resins of formula (I.C) containing a 1,1,3,3-tetramethylguanidine (TMG) function (L=—CH$_2$—, R$_1$=R$_2$=R$_3$=R$_4$=CH$_3$—).

The technique used consists in directly incorporating TMG into a chloromethyl PS-DVB resin, according to the method described in U.S. Pat. Nos. 3,346,516 and 5,028,259.

Two types of chloromethyl PS-DVB resins are used:

a) a resin of gel type: Bio-Beeds® SSX1, based on PS 1% crosslinked with DVB and chloromethylated with a chlorine content of 11.52% by weight relative to the total weight. This resin thus contains 4.09 mmol of Cl/g of resin.

b) A resin of macroporous type which has the following characteristics:

Specific surface: 22.5 m$^2$/g of resin
Average pore diameter: 20 Å
Pore volume: 69% chloromethylated with a chlorine content of 19.32% by weight relative to the total weight.

This resin thus contains 5.44 meq of Cl/g of resin.

Procedure:

A determined amount of dry chloromethyl resin containing 0.0544 mol of Cl (i.e. 13.3 g for resin 1. a) and 10 g for resin 1. b)) is weighed out and placed in contact, under a nitrogen atmosphere, with 12.5 g (0.1088 mol) of TMG diluted in 130 ml of tetrahydrofuran (THF) pre-dried over molecular sieve. The reaction medium thus obtained is stirred mechanically for 48 hours at a temperature of 60° C. After cooling to 20° C., the resin is filtered off and is washed with THF, then with 200 ml of aqueous 10% sodium hydroxide solution and lastly with water until neutral. The resin is washed with acetone and then dried under vacuum at 60° C. to constant weight.

Elemental analysis was carried out on the two resins thus obtained.

For resin a) of gel type referred to hereinbelow as No. 1 (TMG), N=7.85% by weight, i.e. 1.87 mmol of TMG/g of resin.

For resin b) of macroporous type referred to hereinbelow as No. 2 (TMG), N=8.74% by weight, i.e. 2.08 mmol of TMG/g of resin. 2. Production of PS-DVB resins of formula (I.C) containing a TMG function (L=—CH$_2$—O—CH$_2$—CH$_2$—, R$_1$=R$_2$=R$_3$=R$_4$=—CH$_3$). The two resins a) and b) above were used.

a) Preparation of sodium aminoethoxide (NaO—(CH$_2$)$_2$—NH$_2$).

A solution of 2.5 ml of ethanolamine in 25 ml of anhydrous THF (freshly distilled over sodium) is added slowly, under a nitrogen atmosphere, to a solution of 1.5 g of sodium hydride dissolved in 40 ml of anhydrous THF. The reaction medium is kept stirring at a temperature of 20° C. for 1 hour and is then maintained at reflux for 2 hours. The sodium aminoethoxide solution is then cooled to 20° C. and maintained under a nitrogen atmosphere.

b) Production of resins of general formula (A) containing a primary amine function, in which L represents —CH$_2$—O—CH$_2$—CH$_2$—;

A determined amount of the above dry chloromethyl resin 1.

a) containing 0.0272 mol of chlorine, i.e. 6.65 g, is selected.

The same selection is made with the dry chloromethyl resin 1.

b) based on 0.0272 mol of chlorine. i.e. 5 g.

Each of these resins is treated separately as follows:

The resin selected (6.65 or 5 g) is introduced into an aminoethoxide solution prepared according to 2. a). The medium is kept stirring at 70° C. for 48 hours. After cooling to about 20° C., the resin is recovered. It is washed with water, then with aqueous 5% by weight potassium hydroxide solution and then with water until neutral. The wet resin is washed with methanol and finally dried under vacuum at 60° C.

c) Preparation of tetramethylchloroformamidinium chloride

A solution of 2.5 ml (0.027 mol) of oxalyl chloride in 15 ml of anhydrous carbon tetrachloride is poured dropwise into a solution of 3.4 ml (0.027 mol) of tetramethylurea in 10 ml of anhydrous carbon tetrachloride kept stirring under a nitrogen atmosphere. While the stirring is continued, the reaction medium is maintained at reflux until the evolution of carbon dioxide and carbon monoxide gases has ceased. The formamidinium chloride obtained in the form of a white solid is dissolved at 0° C. in 30 ml of anhydrous acetonitrile.

d) Reaction with the above resins containing a primary amine function (L=$CH_2$—O—$CH_2$—$CH_2$—)

For each of the above two resins 5 g of resin are suspended, with stirring and at a temperature of 0° C., in a mixture of 5.2 ml (0.0374 mol) of triethylamine and 20 ml of anhydrous acetonitrile. The solution of formamidinium chloride in 30 ml of anhydrous acetonitrile obtained above is added slowly to this suspension maintained at 0° C. The mixture is stirred for 72 hours at a temperature of 20° C. and is then maintained at reflux for 1 hour. After cooling to 20° C., the resin is filtered off and is washed with water, then with 10% by weight sodium hydroxide solution, and again with water until neutral. The wet resin is washed with methanol, then with acetone and lastly dried under vacuum at 60° C.

Elemental analyses are carried out on the two resins thus obtained and the number of moles of grafted guanidine functions are calculated:

for the resin of gel type obtained from 1. a):

N=9.03%, i.e. 2.15 mmol of tetramethylguanidine (-TMG)/g of resin, referred to hereinbelow as No. 3 (-TMG).

for the resin of macroporous type obtained from 1. b):

N=6.98%, i.e. 1.66 mmol of tetramethylguanidine (-TMG)/g of resin, referred to hereinbelow as No. 4 (-TMG).

3. Production of PS-DVB resins of formula (I.C) containing a 1,1,3,3-tetra-n-butylguanidine (TBG) function (L=—$CH_2$—, $R_1$=$R_2$=$R_3$=$R_4$=n-butyl).

The preparation technique used consists in starting with a non-functionalized PS-DVB resin. This copolymer is functionalized, in a first step, into aminomethyl resin (—$CH_2$—$NH_2$ function) according to the method described in Tetrahedron Letters No. 42, 1976, 3795–3798. The resin obtained is then functionalized into resin containing a 1,1,3,3-tetra-n-butylguanidine function using tetra-n-butylchloroformamidinium chloride.

The PS-DVB resin used is a porous synthetic copolymer manufactured by Rohm and Haas, Amberlite XAD-4. The characteristics of this highly-crosslinked resin, given by Rohm and Haas, are:

Specific surface: 750 m²/g of resin

Average pore diameter: 50 Å

Pore volume: 51%.

a) Functionalization of the Amberlite XAD-4 resin into phthalimidomethyl resin.

10 g of pre-dried Amberlite XAD-4 resin are suspended in a solution of 0.5 ml (0.0043 mol) of tin tetrachloride in 30 ml of 1,2-dichloroethane. 6.7 g (0.0342 mol) of N-chloromethylphthalimide dissolved in 20 ml of 1,2-dichloroethane are added, with stirring and at 60° C., to this suspension. The reaction medium is maintained at reflux (82°–84° C.) with stirring for 5 hours. After cooling to room temperature (20° C.), the resin is filtered off and is then washed with dichloromethane and finally with methanol. After drying at 60° C. under vacuum, 13.1 g of resin are obtained.

IR spectrum: ν (CO—N—CO) and δ (CO—N—CO) at 1770 cm$^{-1}$ and 1710 cm$^{-1}$.

b) Hydrazinolysis to produce the primary amine function.

4.5 ml (0.092 mol) of hydrazine hydrate and 0.9 g (0.022 mol) of sodium hydroxide pellets are added, with stirring, to a suspension of 12 g of the resin obtained in 3. a) in 40 ml of absolute ethanol.

The reaction medium is then maintained at reflux for 48 hours. After cooling to 20° C., the resin is filtered off and is washed with ethanol and then with aqueous 5% by weight potassium hydroxide solution. The resin is then washed with water until neutral, with ethanol, with acetone and lastly with methanol. It is then dried under vacuum at 60° C. to give 11 g of resin. This resin no longer shows the characteristic bands of phthalimide on IR.

An elemental analysis is carried out: N=3.53%, i.e. 2.52 mmol of —$NH_2$/g of resin.

c) Functionalization of this aminomethyl resin into a tetra-n-butylguanidine function.

Tetra-n-butylchloroformamidinium chloride is prepared by bubbling 5.5 g of phosgene into 10.4 g (0.037 mmol) of tetra-n-butylurea over 2 hours, with stirring at a temperature of 80° C. for 5 hours. The excess phosgene is then eliminated by evaporation under vacuum. 12.45 g of tetra-n-butylchloroformamidium chloride are obtained in the form of a white solid.

This chloride is dissolved in 40 ml of anhydrous acetonitrile.

10 g of the aminomethyl resin and 8.7 ml (0.0625 mol) of triethylamine are added, under a nitrogen atmosphere and at 0° C., to this stirred chloride solution. The reaction mixture is kept stirring at 20° C. for 96 hours and is then maintained at reflux for 1 hour. After cooling to 20° C., the resin is filtered off and is washed with acetonitrile and then with aqueous 10% by weight sodium hydroxide solution. It is then washed with water until neutral, with acetone, with methanol and again with acetone. It is dried under vacuum at 60° C. to give 11.3 g of resin.

An elemental analysis is carried out: N=4.62%, i.e. 1.1 mmol of guanidine (-TBG)/g of resin.

This resin is referred to hereinbelow as No. 1 (-TBG).

4. Production of PS-DVB resins of formula (I.D) containing a 1,5,7-triazabicyclo[4.4.0]dec-5-ene (TBD) function with L=—$CH_2$—.

The process used is described in J. Macromol. Sci. Pure. Appl. Chem A29(3) 1992, 249–263.

It consists in reacting the lithium salt of 1,5,7-triazabicyclo[4.4.0]dec-5-ene with a chloromethyl PS-DVB resin.

a) Preparation of the lithium salt of TBD.

0.052 mol of n-butyllithium in 25 ml of hexane is added to a mixture of 7.9 g (0.057 mol) of TBD and 250 ml of anhydrous THF, at a temperature of −78° C. and under an argon atmosphere. The reaction medium is then stirred at −78° C. for 2 hours.

b) Production of the (I.D.) resins containing a TBD function.

A determined amount of chloromethyl resin corresponding to 0.0544 mol of chlorine (i.e. 13.3 g of the gel-type resin 1. a) or 10 g of the macroporous-type resin 1.b)) is weighed out. This amount is added slowly, under an argon atmosphere, to the solution of the lithium salt of TBD maintained at −78° C.

The reaction mixture is then warmed gradually to 20° C. with stirring and is maintained under these conditions for 70 hours. 30 ml of methanol are then added and the resin is filtered off on a sinter funnel. It is washed successively with a 1/1 by volume THF/methanol mixture, then with methanol, with a 1/1 by volume methanol/water mixture, with acetone, with THF and with dichloromethane. The resin is dried under vacuum at 60° C.

Elemental analyses of the two resins thus obtained are carried out.

Resin of gel type:
N=11.88%, i.e. 2.83 mmol of TBD function/g resin.
This resin is referred to hereinbelow as No. 1 (-TBD).

Resin of macroporous type:
N=11.29%, i.e. 2.69 mmol of TBD function/g of resin.
This resin is referred to hereinbelow as No. 2 (-TBD).

EXAMPLE 1

Production of di-n-butyl disulphide by reaction of n-butyl mercaptan with sulphur.

Tests for the production of di-n-butyl disulphide are carried out under identical experimental conditions using resins containing a guanidine function (TMG) or containing a bicyclic guanidine function (TBD).

A commercial Fluka resin is also used, containing a TBD function, L=—CH$_2$—:

No. 90603 from the 1995/96 Fluka catalogue
PS cross-linked with 2% DVB
TBD: 2.8 mmol of TBD/g of dry resin.

Comparative tests are also carried out using a PS-DVB resin of macroporous type containing a tertiary amine function, L=—CH$_2$—, the Amberlyst A-21 resin manufactured by the company Rohm and Haas. Characteristics of the Amberlyst A-21 resin are: Specific surface: 39.8 m$^2$/g of resin functionalized with —CH$_2$—N(CH$_3$)$_2$: 4.4 mmol of tertiary amine function/g of dry resin.

The tests are carried out in a reactor consisting of a 50 ml two-necked glass conical flask fitted with a water-cooled condenser and a thermometer sheath for measuring the temperature of the reaction medium. This reactor is heated by an oil bath placed on the plate of a magnetic hot-plate stirrer. Stirring is obtained in the reactor by means of a teflon-coated magnetic stirrer-bar.

Procedure:

26.58 g (0.295 mol) of n-butyl mercaptan, 4.5 g (0.147 mol) of finely ground solid sulphur and 0.1 g of dry resin are introduced into the reactor. The reaction medium is brought to 60° C. with stirring. After total disappearance of the solid sulphur (generally after 15 min.), samples of the liquid reaction medium are withdrawn at determined times. These samples are analysed by gas chromatography on a Hewlett-Packard Ultra-1 capillary column 50 m in length, to determine the di-n-butyl disulphide (S$_2$%) content by weight formed as a function of time in min.

In the case of tests carried out in the presence of methanol, the amount of methanol incorporated into the reaction mixture is 0.4 g (0.0125 mol). The results are featured in Tables I and II below.

TABLE I

Resins containing a 1,1,3,3-tetramethylguanidine (-TMG) function

| Resin reference Nature Functionality (mmol/g) | (A-21)* Macroporous —CH$_2$—N(CH$_3$)$_2$ 4.4 | No. 1 (-TMG) Gel —CH$_2$-TMG 1.87 | | No. 2 (-TMG) Macroporous —CH$_2$-TMG 2.08 | | No. 3 (-TMG) Gel —CH$_2$—O—CH$_2$—CH$_2$-TMG 2.15 | | No. 4 (-TMG) Macroporous —CH$_2$—O—CH$_2$—CH$_2$-TMG 1.66 | |
|---|---|---|---|---|---|---|---|---|---|
| Time (min.) | S$_2$ % | S$_2$ % | (methanol) S$_2$ % | S$_2$ % | (methanol) S$_2$ % | S$_2$ % | (methanol) S$_2$ % | S$_2$ % | (methanol) S$_2$ % |
| 30 | 54.6 | 58.1 | 64.0 | 68.1 | 56.6 | 58.3 | 67.0 | 66.3 | 56.3 |
| 60 | 58.9 | 65.9 | 70.2 | 75.6 | 75.9 | 67.1 | 75.7 | 75.0 | 72.6 |
| 90 | 65.0 | 70.1 | 75.7 | 80.6 | 82.6 | 71.7 | 79.2 | 82.2 | 81.1 |
| 180 | 72.0 | 76.2 | 79.9 | 83.7 | 85.3 | 78.3 | 85.8 | 84.1 | 84.3 |
| 360 | 79.5 | 81.7 | 84.0 | 84.0 | 87.2 | 81.5 | 85.9 | 84.7 | 84.3 |

*Comparative test

TABLE II

Resins containing a 1,5,7-triazabicyclo[4.4.0]dec-5-ene (-TBD) function

| Resin reference Nature Functionality (mmol/g) | (A-21)* Macroporous —CH$_2$—N(CH$_3$)$_2$ 4.4 | -TBD/Fluka Gel —CH$_2$-TBD 2.8 | | No. 1 (-TBD) Gel —CH$_2$-TBD 2.83 | | No. 2 (-TBD) Macroporous —CH$_2$-TBD 2.69 | |
|---|---|---|---|---|---|---|---|
| Time (min.) | S$_2$ % | S$_2$ % | (methanol) S$_2$ % | S$_2$ % | (methanol) S$_2$ % | S$_2$ % | (methanol) S$_2$ % |
| 30 | 54.6 | d | 59.3 | d | 64.6 | 50.6 | 50.0 |
| 60 | 58.9 | 41.2 | 80.3 | 42.1 | 79.8 | 69.3 | 72.9 |
| 90 | 65.0 | 44.9 | 83.4 | 45.6 | 82.7 | 82.7 | 79.3 |
| 180 | 72.0 | 68.1 | 84.7 | 67.6 | 84.8 | 84.1 | 84.2 |
| 360 | 79.5 | 80.9 | 84.8 | 81.7 | 85.4 | 87.2 | 84.7 | d = Total disappearance of the solid sulphur after 40 min.
*Comparative test

These tables show that the process according to the present invention leads to better results than the prior art.

EXAMPLE 2

Production of di-tert-butyl polysulphides by reaction of tert-butyl mercaptan with sulphur Tests for the production of polysulphides starting with tert-butyl mercaptan and sulphur are carried out in the presence of resins and optionally methanol. A comparative test is carried out with the Amberlyst A-21 resin.

Procedure:

These tests are performed in the same apparatus as in Example 1, under the following identical conditions:

26.5 g (0.294 mol) of tert-butyl mercaptan are introduced, with 18 g (0.56 mol) of finely ground sulphur, into the reactor with stirring and the reaction medium is brought to 60° C.

The time for total disappearance of the sulphur is noted. After reaction for 90 min. a first sample of the liquid reaction medium is withdrawn, followed by other successive withdrawals in the course of time. The samples are analysed by gas chromatography on a Hewlett-Packard Ultra-1 capillary column 50 m in length, to determine their residual tert-butyl mercaptan content, which represents the rate of conversion of this mercaptan into corresponding polysulphides.

Table III below shows the results of these tests, which give, for each resin tested, the time after which all of the solid sulphur has disappeared and the tert-butyl mercaptan content (% TMB by weight) remaining in the reaction medium.

In the case of tests carried out in the presence of methanol, the amount of this alcohol incorporated into the reaction medium is 0.4 g (0.0125 mol).

The tests for the retrogradation of the polysulphides ($S_x$ with x>3) by tert-butyl mercaptan are carried out in the presence of different guanidine resins optionally in the presence of methanol.

A comparative test is carried out with the Amberlyst A-21 resin.

All the tests are performed in an apparatus identical to that described above.

Procedure:

10 g (0.0365 mol) of di-tert-butyl polysulphide, 19.71 g (0.219 mol) of tert-butyl mercaptan and 0.5 g of the chosen resin are introduced into the reactor. The reaction medium is brought quickly to a temperature of 60° C. with stirring. Samples are withdrawn at determined time intervals and are analysed by gas chromatography on a Hewlett-Packard Ultra-1 capillary column 50 m in length.

The chromatographic monitoring makes it possible to determine the di-tert-butyl trisulphide content formed over time.

In the case of the tests carried out in the presence of methanol, the amount of this alcohol incorporated into the reaction medium is 0.4 g (0.0125 mol).

The results of the tests with the different resins tested are featured in Tables IV, V and VI below, which give, for each resin tested, the weight proportion of di-tert-butyl trisulphide ($S_3$%) formed as a function of time in min.

TABLE III

| Resin reference | (A-21)* | | No. 2 (-TMG) | | No. 1 (-TBD) | |
|---|---|---|---|---|---|---|
| Nature | Macroporous | | Macroporous | | Gel | |
| Functionality | —$CH_2$—$N(CH_3)_2$ | | —$CH_2$-TMG | | —$CH_2$-TBD | |
| (mmol/g) | 4.4 | | 2.08 | | 2.83 | |
| | | Methanol | | Methanol | | Methanol |
| Dissolution of the sulphur | 80 min. | 80 min. | 67 min. | 60 min. | No reaction | 45 min. |
| Time (min.) | TBM % | TBM % | TBM % | TBM % | TBM % | TBM % |
| 90 | 4.1 | 4.6 | 6.2 | 3.6 | — | 2.1 |
| 180 | 3.4 | 3.3 | 3.2 | 2.7 | — | 2.0 |

*Comparative test

It is seen that the results of the process according to the invention are better than that of the prior art.

EXAMPLE 3

Production of di-tert-butyl trisulphide by retrogradation by tert-butyl mercaptan of ditert-butyl polysulphides of higher sulphur order The di-tert-butyl polysulphide used has an average molar mass of 250, a sulphur content of 54.4% and a di-tert-butyl trisulphide content, determined by gas chromatography, on a Hewlett-Packard Ultra-1 capillary column 50 m in length, of 29.5%, the remainder consisting of polysulphides of higher sulphur order.

TABLE IV

Resins of gel type containing a guanidine function
(Tests with methanol)

| Resin reference<br>Nature<br>Functionality<br>(mmol/g) | (A-21)*<br>Macroporous<br>—CH$_2$—N(CH$_3$)$_2$<br>4.4 | No. 1 (-TMG)<br>Gel<br>—CH$_2$-TMG<br>1.87 | No. 3 (-TMG)<br>Gel<br>—CH$_2$—O—CH$_2$—CH$_2$-TMG<br>2.15 | No. 1 (-TBD)<br>Gel<br>—CH$_2$-TBD<br>2.83 | -TBD/Fluka<br>Gel<br>—CH$_2$-TBD<br>2.8 |
|---|---|---|---|---|---|
| Time (min.) | S$_3$ % | S$_3$ % | S$_3$ % | S$_3$ % | S$_3$ % |
| 30  | 50.9 | 50.1 | 74.3 | 57.0 | 40.4 |
| 60  | 58.5 | 60.1 | 85.4 | 74.3 | 60.3 |
| 120 | 65.2 | 80.2 | 91.5 | 83.9 | 85.0 |
| 180 | 68.8 | 82.1 | 93.3 | 90.8 | 93.7 |
| 240 | 70.9 | 83.9 | 93.6 | 91.8 | 94.5 |
| 300 | 72.8 | 85.1 | 93.9 | 92.1 | 94.6 |

*Comparative test

TABLE V

Resins of macroporous type containing a guanidine function
(Tests with methanol)

| Resin reference<br>Nature<br>Functionality<br>(mmol/g) | (A-21)*<br>Macroporous<br>—CH$_2$—N(CH$_3$)$_2$<br>4.4 | No. 2 (-TMG)<br>Macroporous<br>—CH$_2$-TMG<br>2.08 | No. 4 (-TMG)<br>Macroporous<br>—CH$_2$—O—CH$_2$—CH$_2$-TMG<br>1.66 | No. 2 (-TBD)<br>Macroporous<br>—CH$_2$-TBD<br>2.69 | No. 1 (-TBG)<br>Macroporous<br>—CH$_2$-TBD<br>1.1 |
|---|---|---|---|---|---|
| Time (min.) | S$_3$ % | S$_3$ % | S$_3$ % | S$_3$ % | S$_3$ % |
| 30  | 50.9 | 51.4 | 60.7 | 55.6 | 42.4 |
| 60  | 58.5 | 74.8 | 83.3 | 75.0 | 68.0 |
| 120 | 6S.2 | 90.9 | 96.6 | 94.4 | 76.8 |
| 180 | 68.8 | 92.3 | 97.1 | 95.2 | 87.1 |
| 240 | 70.9 | 95.7 | 98.5 | 96.S | 91.2 |
| 300 | 72.8 | 96.0 | 98.5 | 96.S | 93.8 |

*Comparative test

TABLE VI

Resins of macroporous type containing a guanidine function
(Tests without methanol)

| Resin reference<br>Nature<br>Functionality<br>(mmol/g) | (A-21)*<br>Macroporous<br>—CH$_2$—N(CH$_3$)$_2$<br>4.4 | No. 2 (-TMG)<br>Macroporous<br>—CH$_2$-TMG<br>2.08 | No. 4 (-TMG)<br>Macroporous<br>—CH$_2$—O—CH$_2$—CH$_2$-TMG<br>1.66 | No. 2 (-TBD)<br>Macroporous<br>—CH$_2$-TBD<br>2.69 | No. 1 (-TBG)<br>Macroporous<br>—CH$_2$-TBG<br>1.1 |
|---|---|---|---|---|---|
| Time (min.) | S$_3$ % | S$_3$ % | S$_3$ % | S$_3$ % | S$_3$ % |
| 30  | 50.9 | 59.2 | 56.3 | 37.7 | 51.7 |
| 60  | 58.5 | 77.4 | 79.4 | 58.8 | 66.0 |
| 120 | 65.2 | 90.5 | 90.6 | 76.7 | 80.9 |
| 186 | 68.8 | 92.8 | 92.9 | 90.1 | 88.7 |
| 240 | 70.9 | 94.7 | 94.7 | 92.3 | 91.9 |
| 300 | 72.8 | 94.7 | 94.7 | 93.9 | 94.5 |

*Comparative test

It is seen from these results that methanol has no positive effect on the reaction in the presence of the Amberlyst A-21 resin (comparative test).

In this reaction for the retrogradation of ditert-butyl polysulphides into di-tert-butyl trisulphide, the resins of gel type with a guanidine function have very low reactivities in the absence of methanol. On the other hand, unexpectedly, the presence of methanol, in low proportion, has a very substantial promoting effect. The effect of methanol is much more attenuated in the case of the resins of macroporous type containing a guanidine function.

The preceding examples can be repeated with similar success by substituting the generically or specifically described reactants and/or operating conditions of this invention for those used in the preceding examples.

The entire disclosure of all applications, patents and publications, cited above and below, and of corresponding French application 95/14582, are hereby incorporated by reference.

From the foregoing description, one skilled in the art can easily ascertain the essential characteristics of this invention, and without departing from the spirit and scope thereof, can make various changes and modifications of the invention to adapt it to various usage and conditions.

What is claimed:

1. In a process for the preparation of organic disulphides and polysulphides by reaction of sulphur with a mercaptan or with a polysulphide of lower sulphur order in order to convert it into polysulphide of higher order, or alternatively by reaction of a mercaptan with an organic polysulphide of a high sulphur order in order to convert it into a polysulphide of lower sulphur order, in the presence of a catalyst in the form of a resin with a basic function, the improvement wherein the resin is based on a polystyrene-divinylbenzene support (PS-DVB), functionalized with basic groups and having the general formula (I):

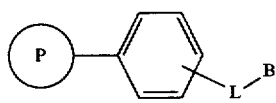
(I)

wherein:

B represents a group selected from a group consisting of: a guanidine radical of formula (C):

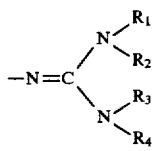
(C)

substituted by L at the imino nitrogen, in which $R_1$, $R_2$, $R_3$ and $R_4$ are, independently of each other, selected from a group consisting of hydrogen and methyl, ethyl, propyl, butyl, cyclohexyl and phenyl groups, with the provision that L represents a linear organic radical which is at least as long as a methylene radical —$CH_2$—, a cyclic guanidine radical of formula (D):

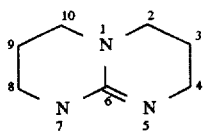
(D)

substituted by L at the 7-position, with the provision that L represents —$(CH_2)_n$—, n being an integer equal to 1 or 3 to 9, a cyclic amidine of formula (E):

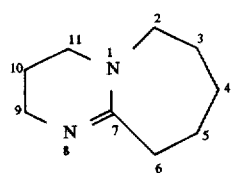
(E)

substituted by L at the 6-position, with the provision that L represents —$(CH_2)_n$—, n being an integer equal to 1 or 3 to 9, and a cyclic amidine of formula (F):

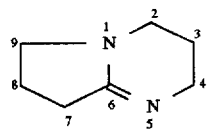
(F)

substituted by L at the 7-position, with the provision that L represents a radical —$(CH_2)_n$—, n being an integer equal to 1 or 3 to 9; and

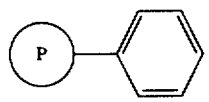

represent the PS-DVB resin support.

2. A process according to claim 1, wherein the resin of general formula (I) is a gel.

3. A process according to claim 1, wherein the resin of general formula (I) is macrocrosslinked and of macroporous structure.

4. A process according to claim 1, wherein L represents methylene (—$CH_2$—).

5. A process according to claim 1, wherein L is attached to the guanidine radical of formula (C), and represents a radical of formula (II)

$$-CH_2-(X-CH_2-CH_2)_m-$$  (II)

X representing oxygen (—O—) or sulphur (—S—) and m is equal to 1 or 2.

6. A process according to claim 5, wherein X represents oxygen and that m is equal to 1.

7. A process according to claim 5, wherein X represents sulphur and m is equal to 1.

8. A process according to claim 1, wherein the mercaptans and organic disulphides and polysulphides have hydrocarbon radicals R selected from a group consisting of alkyl, cycloalkyl, aryl and aralkyl group.

9. A process according to claim 8, wherein the radical R bears at least one functional groups.

10. A process according to claim 1, wherein the resin is present in an amount ranging from 0.01 to 20 parts by weight per 100 parts by weight of reaction mixture, including the resin.

11. A process according to claim 1, wherein the reaction is carried out at a temperature of from −10° C. to 150° C.

12. A process according to claim 11, wherein the temperature is from +10° C. to 120° C.

13. A process according to claim 1, wherein methanol is added to the reaction medium.

14. A process according to claim 4, wherein methanol is added to the reaction medium.

15. A process according to claim 5, wherein methanol is added to the reaction medium.

16. A process according to claim 6, wherein methanol is added to the reaction medium.

17. A process according to claim 7, wherein methanol is added to the reaction medium.

18. A process according to claim 1, wherein a mercaptan is reacted with sulfur to form an organic disulfide.

19. A process according to claim 1, wherein a mercaptan is reacted with sulfur to form an organic polysulfide.

20. A process according to claim 1, wherein a ditertbutyl polysulfide is reacted to form a polysulfide having a lower order of sulfur.

21. A process according to claim 1, wherein B represents the guanidine radical of formula (C).

22. A process according to claim 21, wherein the PS-DVB support is macroporous.

23. A process according to claim 21, wherein the PS-DVB support is a gel.

24. A process according to claim 23, wherein methanol is added to the reaction medium.

25. A process according to claim 21, wherein $R_1$, $R_2$, $R_3$, and $R_4$ are each methyl.

26. A process according to claim 21, wherein $R_1$, $R_2$, $R_3$, and $R_4$ are each n-butyl.

27. A process according to claim 1, wherein B is a radical of formula (D).

* * * * *